United States Patent [19]

Pierce

[11] 4,069,341

[45] Jan. 17, 1978

[54] OXYBIS(4,1-PHENYLENE(2-OXO-2,1-ETHANEDIYL)) THIOCYANATE AND ITS USE AS AN ANTIMICROBIAL AGENT

[75] Inventor: James K. Pierce, Midland, Mich.

[73] Assignee: The Dow Chemical Company, Midland, Mich.

[21] Appl. No.: 733,608

[22] Filed: Oct. 18, 1976

[51] Int. Cl.$^2$ .................. A01N 9/18; C07C 161/04
[52] U.S. Cl. .................................. 424/302; 260/454
[58] Field of Search ..................... 424/302; 260/454

[56] References Cited

U.S. PATENT DOCUMENTS

| 2,281,692 | 5/1942 | Hester et al. | 260/454 |
| 2,937,970 | 5/1960 | Stevenson et al. | 260/454 X |
| 3,697,555 | 10/1972 | Paltauf et al. | 260/454 X |

*Primary Examiner*—Leonard Schenkman
*Attorney, Agent, or Firm*—Daniel DeJoseph; Theodore Post; C. Kenneth Bjork

[57] ABSTRACT

Oxybis(4,1-phenylene(2-oxo-2,1-ethanediyl)) thiocyanate is prepared by reacting diphenyl oxide with chloroacetyl chloride and reacting the intermediate formed thereby with potassium thiocyanate. The compound has antimicrobial utility.

3 Claims, No Drawings

OXYBIS(4,1-PHENYLENE(2-OXO-2,1-ETHANEDIYL)) THIOCYANATE AND ITS USE AS AN ANTIMICROBIAL AGENT

SUMMARY OF THE INVENTION

This invention concerns the compound oxybis(4,1-phenylene(2-oxo-2,1-ethanediyl)) thiocyanate, hereinafter referred to as "Compound", corresponding to the formula

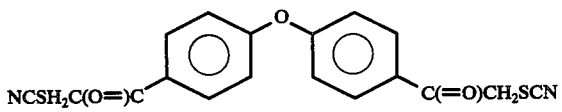

Compound is prepared by reacting diphenyl oxide with chloroacetyl chloride in the presence of alumnium chloride in carbon disulfide reaction medium, whereby 1,1'-(oxydi-4,1-phenylene)bis[2-chloroethanone] is formed. The latter is then reacted with alkali metal thiocyanate, advantageously potassium thiocyanate, in acetone as reaction medium to form Compound.

Compound inhibits the growth of *T. mentagrophytes, M. phlei* and *B. subtilis.*

DESCRIPTION OF SOME PREFERRED EMBODIMENTS

The following additional description and example further describe the invention and the manner and process of making and using it to enable the art-skilled to make and use the same and set forth the best mode contemplated by the inventor of carrying out the invention.

EXAMPLE 1

Diphenyl ether, chloroacetyl chloride, and aluminum chloride in carbon disulfide are allowed to react as described by C. Kunkell, Chem. Zentral., 1768 (1913) to afford intermediate 1,1'-(oxydi-4,1-phenylene)bis[2-chloroethanone]. To prepare Compound, 30.00 g (0.093 mole) of this intermediate was dissolved in 750 ml acetone, 19.83 g (0.204 mole) dry potassium thiocyanate was added thereto in one portion, and the mixture was stirred and allowed to reflux for 3.5 hours, cooled, and poured into 5 liters of ice water. The precipitate was filtered, washed with 1 liter of water, recrystallized from ethanol and dried in a 50° C oven for 16 hours to give Compound as a beige solid, 24.0 g (70% yield), m.p. 129°–130° C. Compound has an elemental analysis, ir spectrum, and nmr spectrum consistent with the assigned structure.

Analysis, percent: Calculated for $C_{18}H_{12}N_2O_3S_2$: C, 58.7; H, 3.28; N, 7.60; S, 17.4. Found: C, 58.6; H, 3.35; N, 7.63; S, 17.3.

ir (CHCl$_3$) — 2130 (—SCN) and 1670 cm$^{-1}$ (—CO).

nmr (CDCl$_3$) — 7.96–6.98 (m, 8, arom) and 4.61 (s, 4, COCH$_2$SCN).

Compound is useful as an antimicrobial for the control of *T. mentagrophytes, M. phlei* and *B. subtilis.* For such uses, Compound can be employed in an unmodified form or together with a carrier, e.g., dispersed on a finely divided solid and employed as a dust. Such mixtures can also be dispersed in water with the aid of a surface-active agent and the resulting emulsions employed as sprays. In other procedures, Compound can be employed as an active constituent in solvent solutions, oil-in-water or water-in-oil emulsions. The augmented compositions are adapted to be formulated as concentrates and subsequently diluted with additional liquid or solid carrier to produce the ultimate treating compositions. Good results are obtained when employing compositions containing antimicrobial concentrations and usually from about 500 to about 1,000 parts by weight of Compound per million parts of such compositions.

Incorporation of Compound into materials which are subject to antimicrobial attack inhibits the growth of the microbes and preserves the original value of the materials. Compound is sufficiently non-volatile and water-insoluble that it will persist on or in such materials for long periods of time. Examples of materials which are adversely effected by microbial growth are latex and alkyd paint films, wood and wooden products. Compound is sufficiently active that only small quantities are required to protect paint films or wood. Compound is therefore useful for long-term protection against microbial growth in or on materials having a wood basis or a protective or decorative paint film subject to microbial attack.

Compound when tested for antimicrobial utility using conventional agar dilution tests gave complete growth inhibition of *Trichophyton mentagrophytes* and *Mycobacterium phlei* at 500 parts per million and 50% inhibition of *Bacillus subtilis*, a bacterium responsible for the deterioration of latex paints, at 500 parts per million.

What is claimed is:

1. Oxybis(4,1-phenylene(2-oxo-2,1-ethanediyl)) thiocyanate.

2. A method of inhibiting the growth of susceptible bacteria and fungi which comprises applying thereto an antimicrobially effective amount of oxybis(4,1-phenylene(2-oxo-2,1-ethanediyl)) thiocyanate.

3. A composition for controlling bacteria and fungi which comprises an antimicrobially effective amount of oxybis(4,1-phenylene(2-oxo-2,1-ethanediyl)) thiocyanate in combination with a carrier.

* * * * *